United States Patent
Seo et al.

(10) Patent No.: US 10,444,139 B2
(45) Date of Patent: Oct. 15, 2019

(54) METHOD AND APPARATUS FOR DISCRIMINATING BETWEEN BLOODSTAINS, AND COMPUTER PROGRAM FOR EXECUTING THE METHOD

(71) Applicant: Republic of Korea (National Forensic Service Director Ministry of Public Administration and Security), Seoul (KR)

(72) Inventors: Young Il Seo, Wonju-si (KR); Eun Bi Lee, Seoul (KR); Sang Yoon Lee, Siheung-si (KR); Eun Ah Joo, Yongin-si (KR); Dong A Lim, Yuseong-gu (KR); Jin Pyo Kim, Yuseong-gu (KR); Nam Kyu Park, Bucheon-si (KR)

(73) Assignee: Republic of Korea (National Forensic Service Director Ministry of Public Administration and Security), Seoul (KR)

( * ) Notice: Subject to any disclaimer, the term of this patent is extended or adjusted under 35 U.S.C. 154(b) by 10 days.

(21) Appl. No.: 15/799,840

(22) Filed: Oct. 31, 2017

(65) Prior Publication Data

US 2019/0003955 A1    Jan. 3, 2019

(30) Foreign Application Priority Data

Jun. 29, 2017 (KR) .................. 10-2017-0082914

(51) Int. Cl.
*G06T 7/00* (2017.01)
*G01N 21/01* (2006.01)
(Continued)

(52) U.S. Cl.
CPC .......... *G01N 21/01* (2013.01); *G06T 7/0012* (2013.01); *G06T 7/60* (2013.01); *G01N 2021/0112* (2013.01)

(58) Field of Classification Search
CPC .............. G01N 33/00; A61B 5/00; G06T 7/00
(Continued)

(56) References Cited

U.S. PATENT DOCUMENTS

| 8,744,231 | B2* | 6/2014 | Lee ...................... A61B 1/0005 386/224 |
| 8,750,952 | B2* | 6/2014 | Aalders ................ A61B 5/0059 600/310 |
| 9,535,016 | B2* | 1/2017 | Xu .................... G01N 23/20066 |

FOREIGN PATENT DOCUMENTS

| KR | 101588323 | 1/2016 |
| KR | 101588322 | 2/2016 |

OTHER PUBLICATIONS

Lee, E., et al., "A study on the maximum distibution angle of the cessation of cast-off bloodstain patterns", Korean Journal of Forensic Sciences, 17, (2016), 87-93.
(Continued)

*Primary Examiner* — Abolfazl Tabatabai
(74) *Attorney, Agent, or Firm* — Schwegman Lundberg & Woessner, P.A.

(57) ABSTRACT

Provided is a method of discriminating between bloodstains, the method including obtaining a captured image of an analysis target; analyzing the captured image and extracting a scattering image of a plurality of bloodstains in the analysis target; estimating a scattering angle of the scattering image; and determining the plurality of bloodstains to be an impact spatter bloodstain if the scattering angle is greater than a preset reference angle, and determining the plurality
(Continued)

of bloodstains to be a cessation cast-off bloodstain if the scattering angle is less than the reference angle.

13 Claims, 7 Drawing Sheets

(51) Int. Cl.
  *G06T 7/60* (2017.01)
  *A61B 5/00* (2006.01)
(58) Field of Classification Search
  USPC .......................................................... 382/131
  See application file for complete search history.

(56) References Cited

OTHER PUBLICATIONS

"Korean Application Serial No. 10-2017-0082914, Notice of Allowance dated Dec. 7, 2017", (w/ English Translation), 8 pgs.

"Korean Application Serial No. 10-2017-0082914, Notice dated Aug. 18, 2017", (w/ English Translation), 4 pgs.

"Korean Application Serial No. 10-2017-0082914, Written Opinion and Amendment filed Oct. 18, 2017 in response to Notice dated Aug. 18, 2017", (w/ English Translation), 8 pgs.

Kim, Soo-Jung, "A Study of Errors in Impact Angle of Blood Droplets and Evaluations in Area of Blood Origin Depending on the Change of Temperature and Humidity", (English Abstract), Korean Journal of Forensic Sciences, vol. 17, No. 1, (2016), 1 pg.

Lee, Geonkang, "Bloodstain Pattern Analysis from the Prediction of Blood Drop Motion Depend on Non-dimensional Numbers", (w/ English Abstract), (2017), p. 118.

Kim, Soo-Jung, "A Study of Errors in Impact Angle of Blood Droplets and Evaluations in Area of Blood Origin Depending on the Change of Temperature and Humidity", (w English Abstract), Korean Journal of Forensic Sciences, 17(1), (2016), 44-50.

Lee, Geonkang, "Bloodstain Pattern Analysis from the Prediction of Blood Drop Motion Depend on Non-dimensional Numbers", (w English Abstract), Proceedings of the KSME Conference, 2013.12, (2013), 118-123.

\* cited by examiner

METHOD AND APPARATUS FOR DISCRIMINATING BETWEEN BLOODSTAINS, AND COMPUTER PROGRAM FOR EXECUTING THE METHOD

CROSS-REFERENCE TO RELATED APPLICATION

This application claims the benefit of Korean Patent Application No. 10-2017-0082914, filed on Jun. 29, 2017, in the Korean Intellectual Property Office, the disclosure of which is incorporated herein in its entirety by reference.

BACKGROUND

1. Field

One or more embodiments relate to a method of discriminating between bloodstains, a bloodstain discriminating apparatus, and a computer program for executing the method.

2. Description of the Related Art

At a crime scene with bloodshed, an analysis of a bloodstain pattern serves an important role in presuming an act. A bloodstain is classified into an impact spatter bloodstain and a cessation cast-off bloodstain. In this regard, the impact spatter bloodstain refers to a bloodstain resulting from blood spattered when a blood pool such as a bleeding site is hit with a blunt weapon. The cessation cast-off bloodstain refers to a bloodstain resulting from blood spattered due to inertia when a swing motion of a bloodstained crime weapon is stopped. Because the impact spatter bloodstain and the cessation cast-off bloodstain have similar patterns, it is highly difficult to discriminate between the patterns at the crime scene.

SUMMARY

One or more embodiments include a method of discriminating between bloodstains, a bloodstain discriminating apparatus, and a computer program for executing the method. In more detail, the one or more embodiments include a method of discriminating between an impact spatter bloodstain and a cessation cast-off bloodstain by measuring an angle of spattered bloodstains, a bloodstain discriminating apparatus, and a computer program for executing the method.

Additional aspects will be set forth in part in the description which follows and, in part, will be apparent from the description, or may be learned by practice of the presented embodiments.

According to one or more embodiments, a method of discriminating between bloodstains includes obtaining a captured image of an analysis target; analyzing the captured image and extracting a scattering image of a plurality of bloodstains in the analysis target; estimating a scattering angle of the scattering image; and determining the plurality of bloodstains to be an impact spatter bloodstain if the scattering angle is greater than a preset reference angle, and determining the plurality of bloodstains to be a cessation cast-off bloodstain if the scattering angle is less than the reference angle.

The extracting of the scattering image may include estimating a scattering direction by using widths and lengths of the plurality of bloodstains in the analysis target.

The estimating of the scattering angle of the scattering image may include generating a first reference line and a second reference line in outer areas of the scattering image by using the scattering direction, the first reference line and the second reference line facing different directions; and estimating the scattering angle by measuring an angle between the first reference line and the second reference line.

The estimating of the scattering angle of the scattering image may further include externally displaying the first reference line and the second reference line; and adjusting positions of the first reference line and the second reference line, in response to an external input.

The method may further include storing actually-measured angles corresponding to types of a crime weapon, wherein the reference angle may be a largest actually-measured angle from among the actually-measured angles.

If the scattering angle is less than the reference angle, the method may further include predicting a type of the crime weapon by comparing the scattering angle with the actually-measured angles.

According to one or more embodiments, there is provided a computer program stored in a medium for executing the method, by using a computer.

According to one or more embodiments, a bloodstain discriminating apparatus includes a camera unit configured to capture an image of an analysis target and to generate the captured image; an image extractor configured to analyze the captured image and to extract a scattering image of a plurality of bloodstains in the analysis target; a scattering angle estimator configured to estimate a scattering angle of the scattering image from the scattering image; a bloodstain determiner configured to determine the plurality of bloodstains to be an impact spatter bloodstain if the scattering angle is greater than a preset reference angle, and to determine the plurality of bloodstains to be a cessation cast-off bloodstain if the scattering angle is less than the reference angle; and a display configured to externally display a result of the determination by using the bloodstain determiner.

The image extractor may be further configured to estimate a scattering direction by using widths and lengths of the plurality of bloodstains in the analysis target.

The scattering angle estimator may be further configured to generate a first reference line and a second reference line in outer areas of the scattering image by using the scattering direction, the first reference line and the second reference line facing different directions, and to estimate the scattering angle by measuring an angle between the first reference line and the second reference line.

The bloodstain discriminating apparatus may further include a user command recognizer configured to recognize a user input, wherein the scattering angle estimator may be further configured to adjust positions of the first reference line and the second reference line, in response to the user input recognized by the user command recognizer, and to estimate the scattering angle by measuring an angle between the first reference line and the second reference line that have been adjusted.

The bloodstain discriminating apparatus may further include a database configured to store actually-measured angles corresponding to types of a crime weapon, wherein the reference angle may be a largest actually-measured angle from among the actually-measured angles.

If the scattering angle is less than the reference angle, the bloodstain determiner may be further configured to predict a type of the crime weapon by comparing the scattering angle with the actually-measured angles.

Aspects, features, and advantages other than the aforementioned descriptions may be understood more readily by reference to the accompanying drawings, claims, and the following detailed descriptions of embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

As the disclosure allows for various changes and numerous embodiments, particular embodiments will be illustrated in the drawings and described in detail in the written description. Effects and features of the disclosure and methods of accomplishing the same may be understood more readily by reference to the following detailed description of embodiments and the accompanying drawings. The disclosure may, however, be embodied in many different forms and should not be construed as being limited to the embodiments set forth herein.

Reference will now be made in detail to embodiments of the present disclosure, examples of which are illustrated in the accompanying drawings, wherein components that are the same or are in correspondence are rendered the same reference numeral regardless of the figure number, and redundant explanations are omitted.

Throughout the specification, while such terms as "first," "second," etc., may be used to describe various components, such components must not be limited to the above terms. The above terms are used only to distinguish one component from another.

Throughout the specification, a singular form may include plural forms, unless there is a particular description contrary thereto.

Throughout the specification, it will be further understood that the terms "comprise", "include," and/or "have," when used in this specification, specify the presence of stated features, and/or components, but do not preclude the presence or addition of one or more other features, and/or components.

Throughout the specification, it will also be understood that when a layer, a region, an element, or the like is referred to as being "on" another layer, region, or element, it can be directly on the other layer, region, or element, or intervening layer, region, or element may also be present.

In the drawings, the thicknesses of layers and regions are exaggerated for clarity. For example, the thicknesses and sizes of elements in the drawings are arbitrarily shown for convenience of description, thus, the spirit and scope of the present disclosure are not necessarily defined by the drawings.

Also, it should also be noted that in some alternative implementations, the steps of all methods described herein may occur out of the order. For example, two steps illustrated in succession may in fact be executed substantially concurrently or the two steps may sometimes be executed in the reverse order.

Throughout the specification, it will also be understood that when a layer, a region, an element, or the like is referred to as being "connected to" or "coupled with" another layer, region, or element, it can be directly connected to or coupled with the other layer, region, or element, or it can be indirectly connected to or coupled with the other layer, region, or element by having an intervening layer, region, or element interposed therebetween. For example, throughout the specification, when a layer, a region, an element, or the like is referred to as being "electrically connected to" or "electrically coupled with" another layer, region, or element, it can be electrically connected to or coupled with the other layer, region, or element in a direct manner, or it can be electrically connected to or coupled with the other layer, region, or element in an indirect manner by having an intervening layer, region, or element interposed therebetween.

As used herein, the term "and/or" includes any and all combinations of one or more of the associated listed items.

Figure 1:
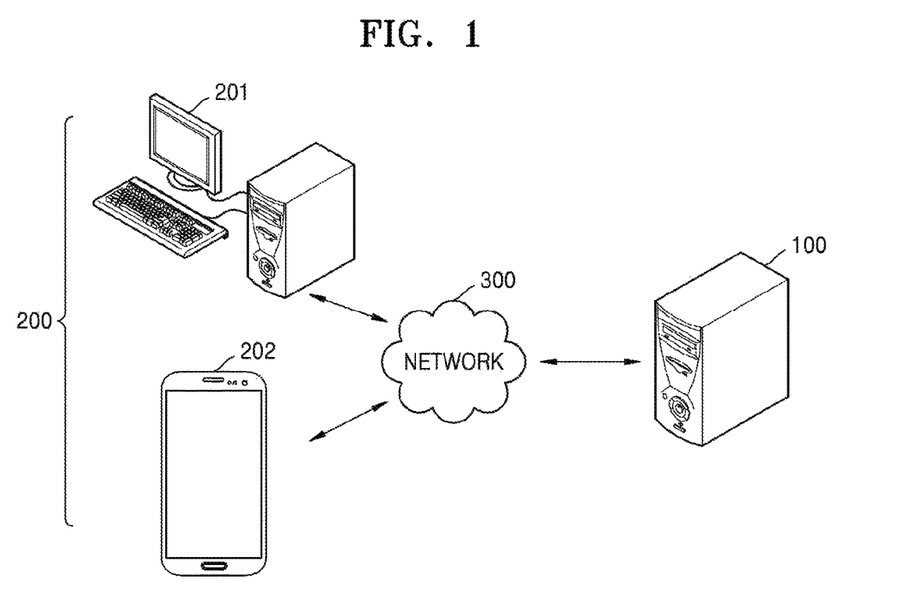
FIG. 1 illustrates a bloodstain discriminating system, according to an embodiment.

FIG. 1 illustrates a bloodstain discriminating system, according to an embodiment.

Referring to FIG. 1, the bloodstain discriminating system according to the present embodiment includes a server 100, a user terminal 200, and a network 300 connecting them.

The bloodstain discriminating system according to the present embodiment provides a bloodstain discriminating service. In more detail, the bloodstain discriminating system according to the present embodiment may upload data obtained by a user based on an experiment or a method of discriminating between bloodstains to be described below, and may share the uploaded data with other users. For example, the user may actually measure angles of scattered bloodstains according to types of a crime weapon, and may upload data of the actually-measured angles. When the user uploads the data, the bloodstain discriminating system according to the present embodiment registers the data in the server 100, and provides an interface for other users to find the data registered in the server 100. Through the aforementioned process, the bloodstain discrimination system according to the present embodiment may form a database of the actually-measured angles of the scattered bloodstains according to the types of a crime weapon.

The user terminal 200 refers to a communication terminal having a camera unit and a touchscreen, and capable of using a web service in a wired or wireless communication environment. In this regard, the user terminal 200 may be a personal computer 201 of the user or a portable terminal 202 of the user. Referring to FIG. 1, the portable terminal 202 is a smartphone, but the present disclosure is not limited thereto, and any terminal to which an application having programmed therein the method of discriminating between bloodstains according to an embodiment can be installed and that has a camera unit may be used without limitation.

The user terminal 200 further includes a display displaying an execution screen, and an input device receiving an input of data from the user. For example, the input device may include, but is not limited to, a keyboard, a mouse, a trackball, a microphone, at least one button, a touch panel, or the like.

The network 300 is configured to connect the user terminal 200 to the server 100. For example, the network 300 provides a connection path for the user terminal 200 to transmit and receive packet data to and from the server 100 after the user terminal 200 accesses the server 100.

Although not illustrated in the drawings, the server 100 according to the present embodiment may include a memory, an input/output unit, a program storing unit, a controller, or the like.

Figure 2:
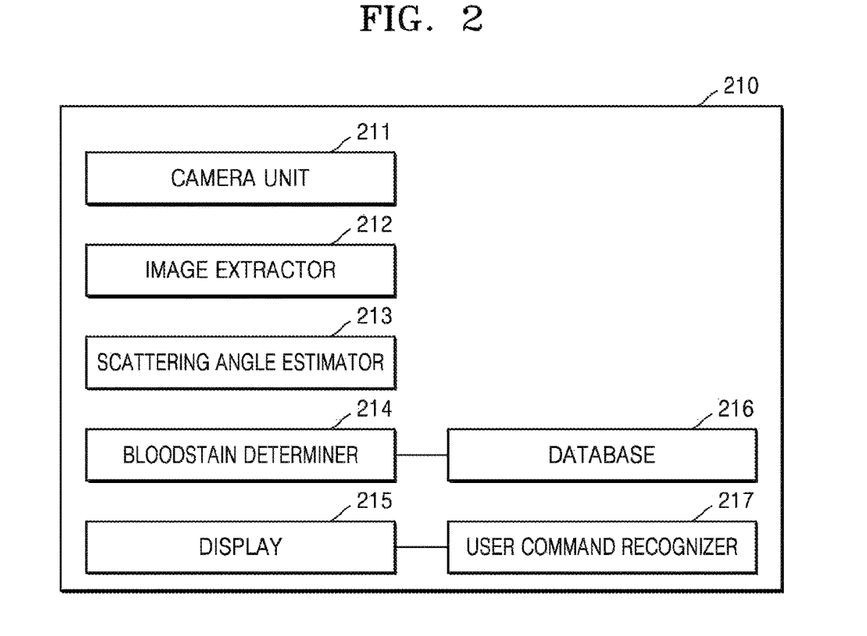
FIG. 2 is a block diagram of a bloodstain discriminating apparatus included in a user terminal illustrated in FIG. 1.

FIG. 2 is a block diagram of a bloodstain discriminating apparatus 210 included in the user terminal 200 illustrated in FIG. 1.

The bloodstain discriminating apparatus 210 according to an embodiment may correspond to at least one processor or may include at least one processor. Thus, the bloodstain discriminating apparatus 210 may operate as a unit included in a hardware device such as a microprocessor or a general-use computer system. The bloodstain discriminating apparatus 210 may be mounted in the user terminal 200 illustrated in FIG.

In order to prevent obscuring features of the present embodiment with unnecessary detail, the bloodstain discriminating apparatus 210 illustrated in FIG. 2 only includes elements related to the present embodiment. However, it is obvious to one of ordinary skill in the art that more general-use elements than the elements illustrated in FIG. 2 may be further included in the bloodstain discriminating apparatus 210.

Referring to FIG. 2, the bloodstain discriminating apparatus 210 according to the present embodiment may include a camera unit 211, an image extractor 212, a scattering angle estimator 213, a bloodstain determiner 214, a display 215, a database 216, and a user command recognizer 217.

The camera unit 211 may capture an image of an analysis target and thus may generate the captured image. The analysis target may refer to a certain area where there are bloodstains at a crime scene.

The user command recognizer 217 recognizes an input signal input to the user terminal 200 by a user. The user may input the input signal to a touchscreen of the user terminal 200. The input signal input by the user may correspond to a user command.

The image extractor 212 may analyze the captured image and thus may extract a scattering image of a plurality of bloodstains in the analysis target. The image extractor 212 may distinguish between the plurality of bloodstains and a background image included in the captured image, and may extract the scattering image of the plurality of bloodstains which is outlined by outermost bloodstains from among the plurality of bloodstains. In this regard, the image extractor 212 may estimate a scattering direction by using widths and lengths of the plurality of bloodstains in the analysis target.

The scattering angle estimator 213 may estimate a scattering angle of the scattering image from the extracted scattering image. The scattering angle estimator 213 may generate a first reference line and a second reference line in outer areas of the scattering image by using the scattering direction, the first reference line and the second reference line facing different directions. The scattering angle estimator 213 may estimate the scattering angle by measuring an angle between the first reference line and the second reference line.

In this regard, the first reference line and the second reference line may be externally displayed on the display 215, so that the user may check them. The user may compare the generated first and second reference lines with the scattering image, and if not correct, the user may adjust positions of the first reference line and the second reference line by touching them. In this regard, the scattering angle estimator 213 may adjust the positions of the first reference line and the second reference line, according to the input recognized by the user command recognizer 217, and may measure an angle between the adjusted first reference line and the adjusted second reference line, thereby estimating the scattering angle.

The bloodstain determiner 214 may determine the plurality of bloodstains as an impact spatter bloodstain if the estimated scattering angle is greater than a preset reference angle, and may determine the plurality of bloodstains as a cessation cast-off bloodstain if the scattering angle same the reference angle or is less than the reference angle. The bloodstain discriminating apparatus 210 according to the present embodiment may further include the database 216 that stores actually-measured angles corresponding to types of a crime weapon. The bloodstain determiner 214 may set a largest actually-measured angle to be the reference angle, the largest actually-measured angle being from among the actually-measured angles stored in the database 216, and may determine bloodstains. In addition, if the scattering angle is less than the reference angle, the bloodstain determiner 214 may predict a type of a crime weapon by comparing the scattering angle with an actually-measured angle. A result of the determination may be externally displayed on the display 215.

Figure 3:
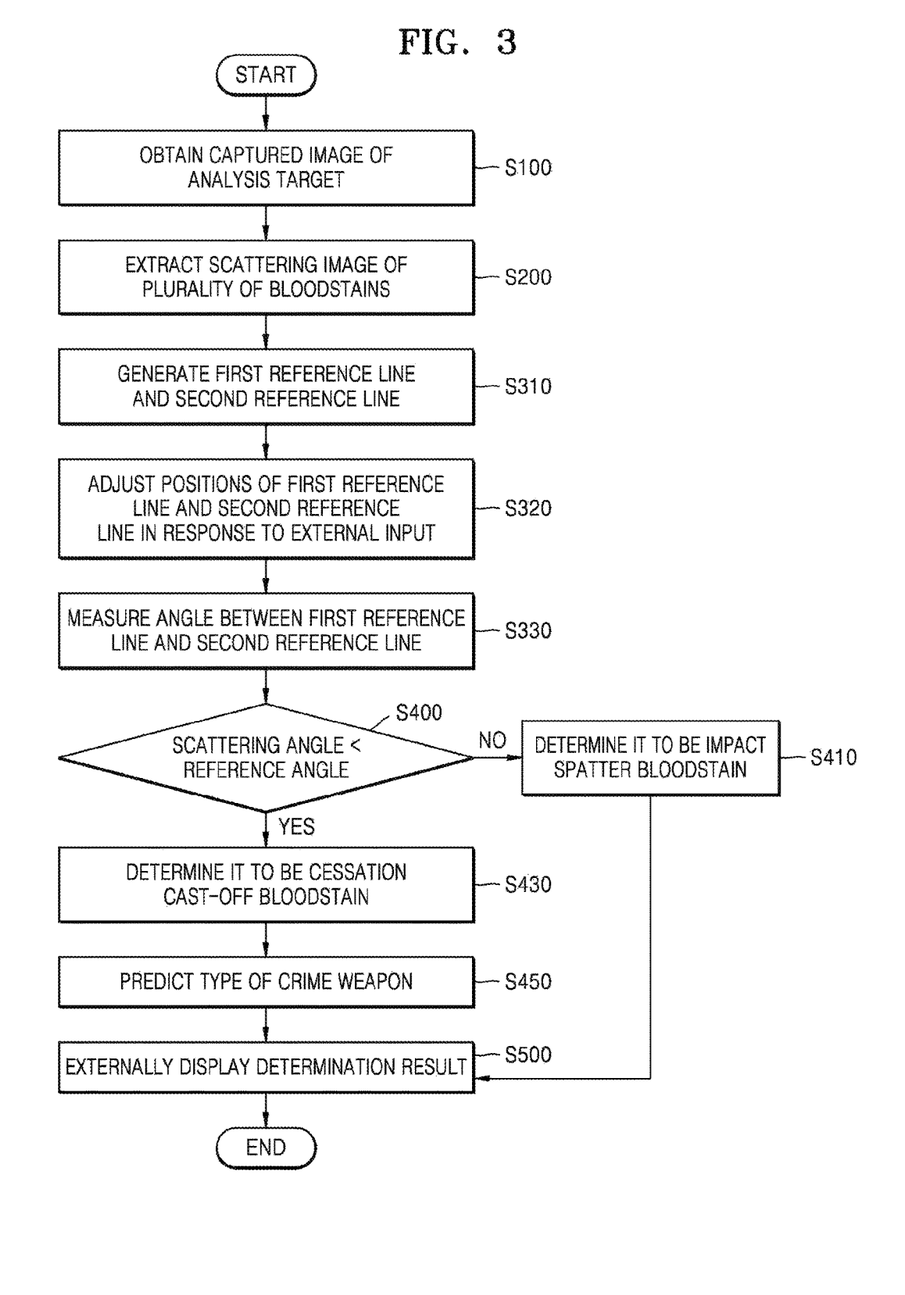
FIG. 3 is a flowchart of a method of discriminating between bloodstains, according to an embodiment.
Figure 4A:
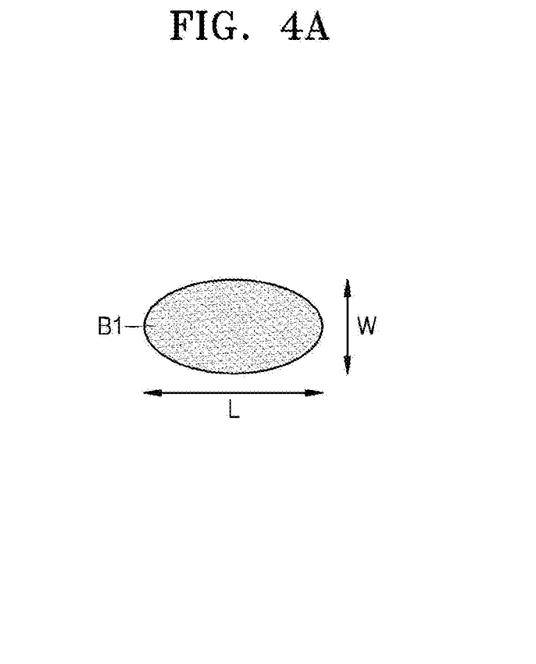
FIGS. 4A and 4B illustrate examples for describing embodiments of the method of estimating a scattering direction using a form of the plurality of bloodstains.
Figure 4B:
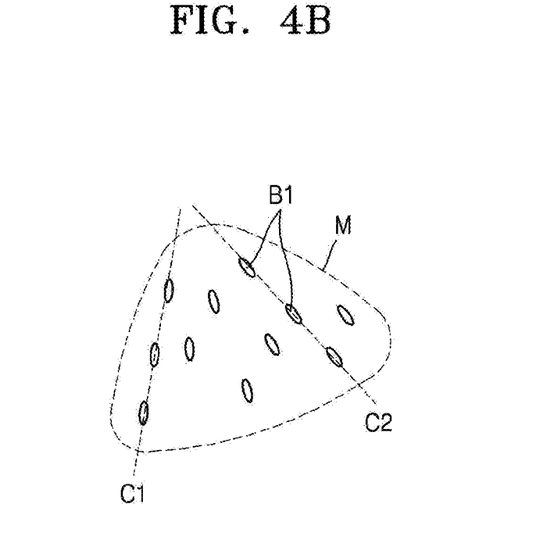
Figure 5:
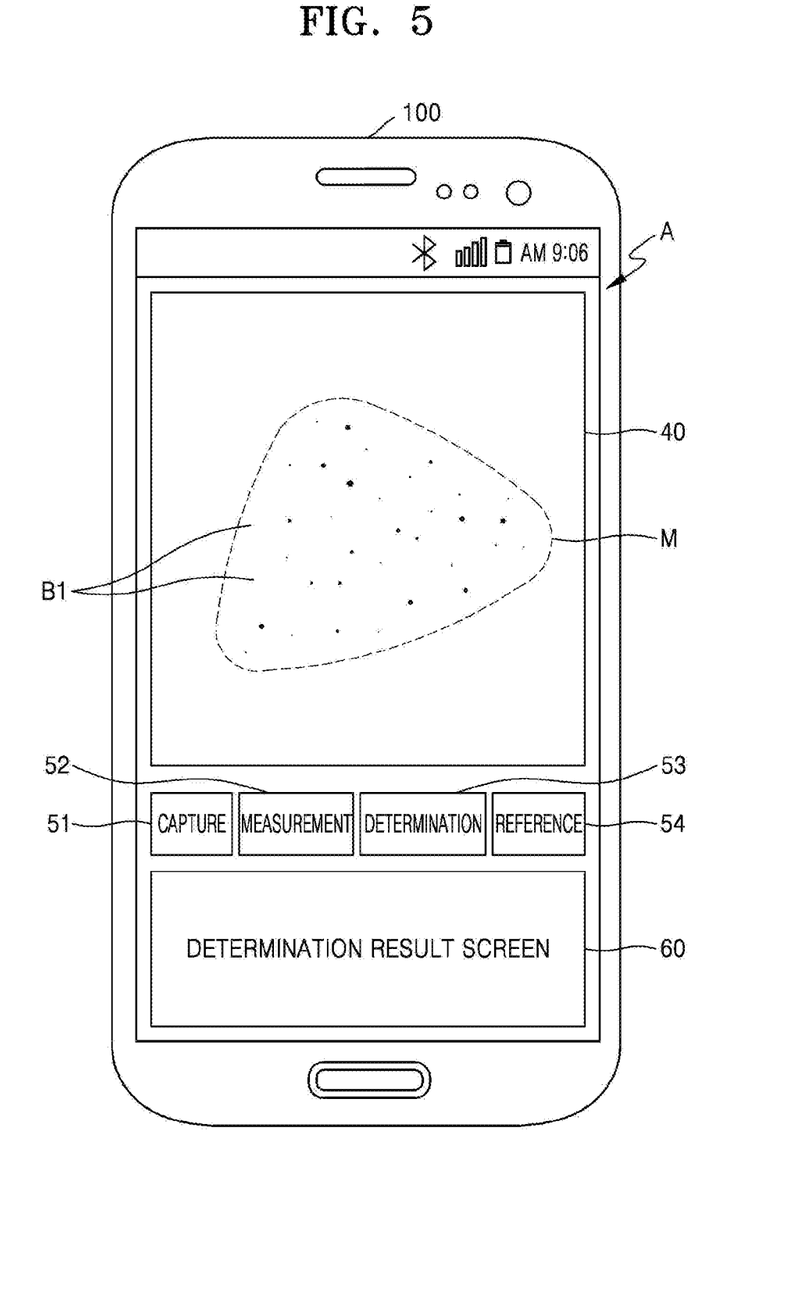
FIGS. 5 through 8 illustrate examples for describing embodiments of the method of discriminating between bloodstains of FIG. 3.

FIG. 3 is a flowchart of a method of discriminating between bloodstains, according to an embodiment, and FIGS. 4A and 4B illustrate examples for describing embodiments of the method of estimating a scattering direction using a form of the plurality of bloodstains. And FIGS. 5 through 8 illustrate examples for describing embodiments of the method of discriminating between bloodstains of FIG. 3.

Referring to FIGS. 3 and 4, first, the bloodstain discriminating apparatus 210 obtains a captured image 40 of an analysis target (S100). In this regard, the captured image 40 may be obtained by directly capturing an image at a crime scene by using the camera unit 211, or may be obtained by retrieving the previously-obtained captured image 40 from a storage (not shown). Alternatively, the captured image 40 may be obtained by downloading the captured image 40 from the server 100 of the bloodstain discriminating system. When the image is directly captured at the crime scene by using the camera unit 211, the user may obtain the captured image 40 by touching a capture button 51 displayed on an execution screen A.

When the captured image 40 is obtained, the obtained captured image 40 is analyzed and thus a scattering image of a plurality of bloodstains in the analysis target is extracted (S200). In this regard, the analysis target may refer to a certain area where the bloodstains are present at the crime scene. The captured image 40 may be divided into the plurality of bloodstains and a background image. In this regard, the image extractor 212 may segment the captured image 40 into unit areas, and may distinguish between the background image and the plurality of bloodstains by using colors of the unit areas or a difference between grayscale values. The image extractor 212 may extract a scattering image M outlined due to the method by outermost bloodstains from among the plurality of bloodstains.

Referring to FIG. 4A, the extracting of the scattering image (S200) may involve estimating a scattering direction by using a width W and a length L of each of a plurality of bloodstains B1 in an analysis target. When each bloodstain B1 that flew with the width W crashes on a wall or a floor, the bloodstain B1 forms the length L due to the impact. In other words, the plurality of bloodstains B1 are scattered in a particular direction from a blood source where the plurality of bloodstains B1 were generated, and thus scattering directions C1 and C2 may be estimated by using a form of the plurality of bloodstains B1 each having the width W and the length L.

Figure 6:
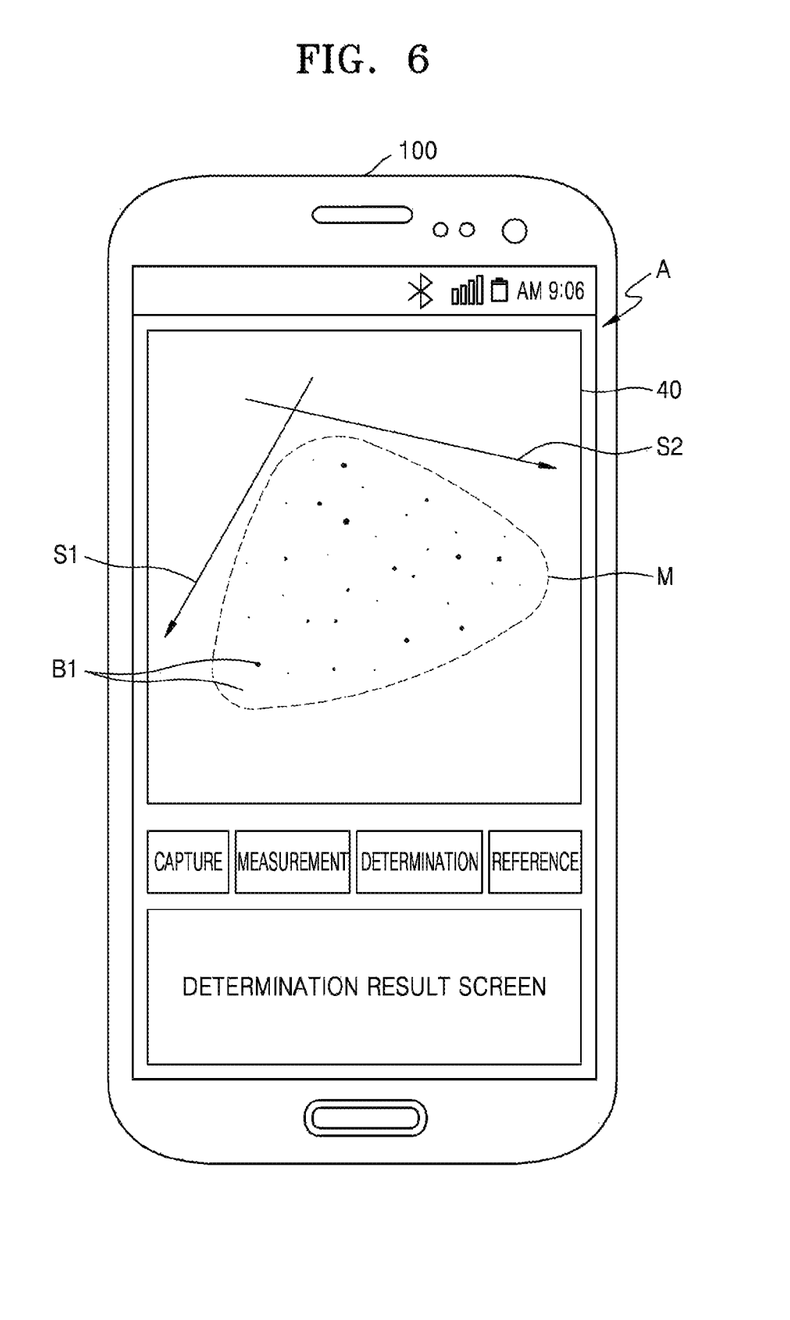

Afterward, referring to FIGS. 3 and 6, the scattering angle of the scattering image M is estimated. In this regard, by using the scattering directions C1 and C2 estimated according to the aforementioned method, a first reference line S1 and a second reference line S2 that face different directions are generated in outer areas of the scattering image M (S310). The generated first reference line S1 and the generated second reference line S2 may be displayed on the execution screen A over the captured image 40. When the user determines that the first reference line S1 and the second reference line S2 displayed on the execution screen A match a bloodstain scattering pattern, the user touches a measurement button 52. In another embodiment, when the user determines that the first reference line S1 and the second reference line S2 displayed on the execution screen A are different from the bloodstain scattering pattern, the user touches the execution screen A, thereby adjusting positions of the first reference line S1 and the second reference line S2 (S320). Afterward, the user touches the measurement button 52 displayed on the execution screen A, so that the scattering angle of the scattering image M is measured (S330).

Next, the estimated scattering angle is compared with a reference angle (S400). In this regard, if the estimated scattering angle is greater than a preset reference angle, the bloodstain discriminating apparatus 210 determines the plurality of bloodstains to be an impact spatter bloodstain (S410), and if the scattering angle is less than the preset reference angle, the bloodstain discriminating apparatus 210 determines the plurality of bloodstains to be a cessation cast-off bloodstain (S430). With respect to the impact spatter bloodstain, when an impact is downwardly applied to a target with a crime weapon, bloodstains splash in almost all directions around a bleeding site. In contrast, with respect to the cessation cast-off bloodstain, the crime weapon is swung in one direction and then is stopped, thus, there is a limit to a scattering angle. Therefore, if the scattering angle of the scattering image M which indicates a scattering degree of bloodstains is greater than the reference angle, it may be determined to be an impact spatter bloodstain, and if the scattering angle of the scattering image M is less than the reference angle, it may be determined to be a cessation cast-off bloodstain.

In this regard, the method of discriminating between bloodstains according to the present embodiment may further include storing actually-measured angles corresponding to types of a crime weapon. An actually-measured angle may refer to a scattering angle obtained by arbitrarily making a scattering of cessation cast-off bloodstains by using a crime weapon such as a knife, a hammer, a hand axe, a baseball bat, etc., and then measuring a scattering degree of the bloodstains. The actually-measured angle may vary according to types of a crime weapon, and its results according to experiments may be stored in a database. Thus, the reference angle may be a largest actually-measured angle from among actually-measured angles. In other words, since the actually-measured angle refers to the scattering angle with respect to the cessation cast-off bloodstains, if the estimated scattering angle is greater than the actually-measured angles obtained according to the experiments using various crime weapons, the plurality of bloodstains may be determined to be an impact spatter bloodstain.

If the estimated scattering angle is less than the reference angle, a type of a crime weapon may be predicted by comparing the scattering angle with the actually-measured angles (S450). For example, an actually-measured angle of a case using a knife may be 78 degrees, an actually-measured angle of a case using a baseball bat may be 80 degrees, and an actually-measured angle of a case using a spanner may be 125 degrees. When the estimated scattering angle is 125 degrees, it is possible to presume that the plurality of bloodstains are not a cessation cast-off bloodstain generated due to a knife, a baseball bat, etc. However, it is not possible to presume that the plurality of bloodstains are not a cessation cast-off bloodstain generated due to a spanner.

Figure 7:
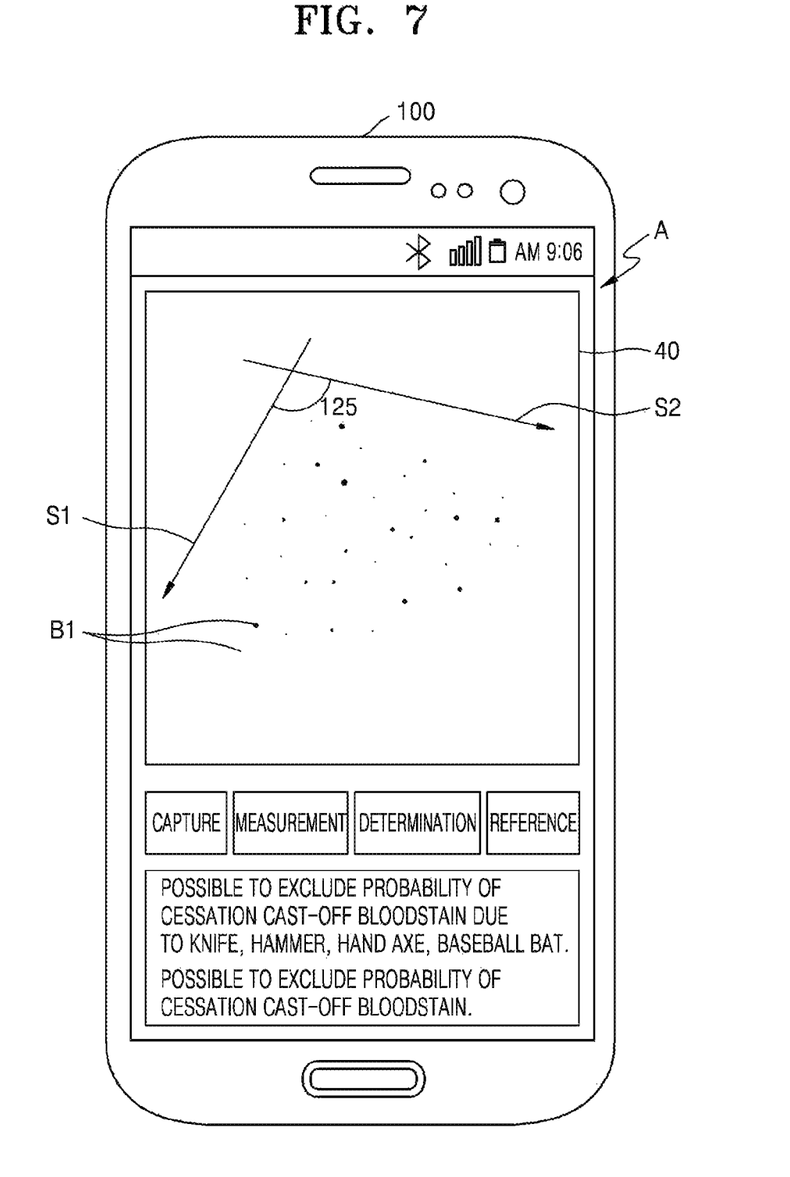
Figure 8:
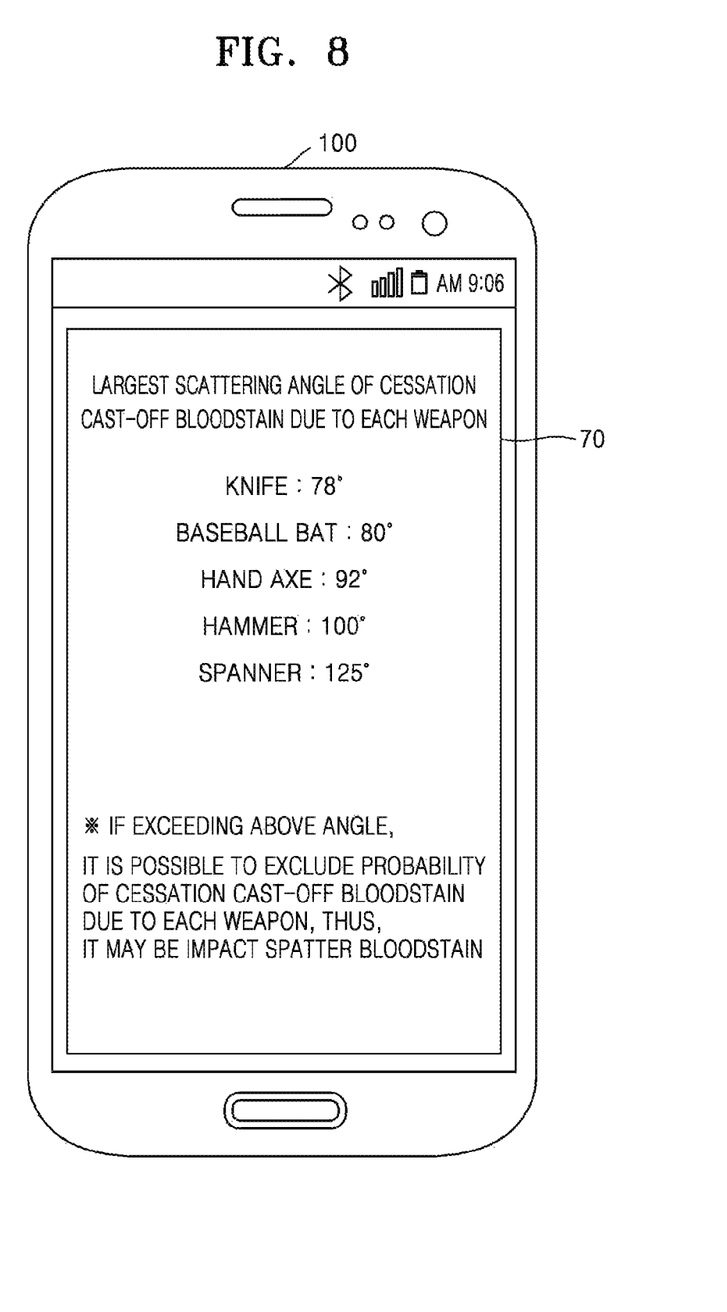

Referring to FIGS. 3 and 7, a determination result 60 of using the aforementioned method is displayed on the execution screen A (S500). When a user touches a determination button 53 displayed on the execution screen A, the determination result 60 may be externally displayed so that the user may check the determination result 60. When the user touches a reference button 54 displayed on the execution screen A, as illustrated in FIG. 8, actually-measured angle data 70 corresponding to types of a crime weapon may be displayed on the execution screen A.

The method of discriminating between bloodstains according to the present embodiment illustrated in FIG. 3 can be written as computer programs and can be implemented in general-use digital computers that execute the programs using a computer-readable recording medium. Examples of the computer-readable recording medium include magnetic storage media (e.g., ROM, floppy disks, hard disks, etc.), optical recording media (e.g., CD-ROMs, or DVDs), etc.

As described above, the method and apparatus for discriminating between bloodstains, and a computer program for executing the method according to the embodiments facilitate discrimination between an impact spatter bloodstain and a cessation cast-off bloodstain that serve an important role in presuming an act at a crime scene.

As described above, the method and apparatus for discriminating between bloodstains, and a computer program for executing the method according to the embodiments facilitate discrimination between an impact spatter bloodstain and a cessation cast-off bloodstain that serve an important role in presuming an act at a crime scene.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of discriminating between bloodstains, the method comprising:
   obtaining a captured image, using a camera unit, of an analysis target;
   analyzing the captured image and extracting a scattering image, using an image extractor, of a plurality of bloodstains in the analysis target;
   estimating a scattering angle, using a scattering angle estimator, of the scattering image; and
   determining, using a bloodstain determiner, the plurality of bloodstains to be an impact spatter bloodstain if the scattering angle is greater than a preset reference angle, and determining, using the bloodstain determiner, the plurality of bloodstains to be a cessation cast-off bloodstain if the scattering angle is less than the reference angle.

2. The method of claim 1, wherein the extracting of the scattering image comprises estimating a scattering direction by using widths and lengths of the plurality of bloodstains in the analysis target.

3. The method of claim 2, wherein the estimating of the scattering angle of the scattering image comprises:
   generating a first reference line and a second reference line in outer areas of the scattering image by using the scattering direction, the first reference line and the second reference line facing different directions; and
   estimating the scattering angle by measuring an angle between the first reference line and the second reference line.

4. The method of claim 3, wherein the estimating of the scattering angle of the scattering image further comprises:
   externally displaying the first reference line and the second reference line; and
   adjusting positions of the first reference line and the second reference line, in response to an external input.

5. The method of claim 1, further comprising storing actually-measured angles corresponding to types of a crime weapon, wherein the reference angle is a largest actually-measured angle from among the actually-measured angles.

6. The method of claim 5, further comprising, if the scattering angle is less than the reference angle, predicting a type of the crime weapon by comparing the scattering angle with the actually-measured angles.

7. A computer program stored in a medium for executing the method of claim 1, by using a computer.

8. A bloodstain discriminating apparatus comprising:
   a camera unit configured to capture an image of an analysis target and to generate the captured image;
   an image extractor configured to analyze the captured image and to extract a scattering image of a plurality of bloodstains in the analysis target;
   a scattering angle estimator configured to estimate a scattering angle of the scattering image from the scattering image;
   a bloodstain determiner configured to determine the plurality of bloodstains to be an impact spatter bloodstain if the scattering angle is greater than a preset reference angle, and to determine the plurality of bloodstains to be a cessation cast-off bloodstain if the scattering angle is less than the reference angle; and
   a display configured to externally display a result of the determination by using the bloodstain determiner.

9. The bloodstain discriminating apparatus of claim 8, wherein the image extractor is further configured to estimate a scattering direction by using widths and lengths of the plurality of bloodstains in the analysis target.

10. The bloodstain discriminating apparatus of claim 9, wherein the scattering angle estimator is further configured to generate a first reference line and a second reference line in outer areas of the scattering image by using the scattering direction, the first reference line and the second reference line facing different directions, and
   estimate the scattering angle by measuring an angle between the first reference line and the second reference line.

11. The bloodstain discriminating apparatus of claim 10, further comprising a user command recognizer configured to recognize a user input,
   wherein the scattering angle estimator is further configured to adjust positions of the first reference line and the second reference line, in response to the user input recognized by the user command recognizer, and to estimate the scattering angle by measuring an angle between the first reference line and the second reference line that have been adjusted.

12. The bloodstain discriminating apparatus of claim 8, further comprising a database configured to store actually-measured angles corresponding to types of a crime weapon, wherein the reference angle is a largest actually-measured angle from among the actually-measured angles.

13. The bloodstain discriminating apparatus of claim 12, wherein, if the scattering angle is less than the reference angle, the bloodstain determiner is further configured to predict a type of the crime weapon by comparing the scattering angle with the actually-measured angles.

* * * * *